United States Patent [19]

Ireland

[11] Patent Number: 4,536,155
[45] Date of Patent: Aug. 20, 1985

[54] DENTAL MATRIX BAND

[76] Inventor: Edward J. Ireland, 925 Burdette St., New Orleans, La. 70118

[21] Appl. No.: 611,011
[22] PCT Filed: Sep. 15, 1983
[86] PCT No.: PCT/US83/01401
  § 371 Date: May 17, 1984
  § 102(e) Date: May 17, 1984
[87] PCT Pub. No.: WO84/01100
  PCT Pub. Date: Mar. 29, 1984

Related U.S. Application Data

[63] Continuation-in-part of Ser. No. 419,220, Sep. 17, 1982, abandoned.

[51] Int. Cl.³ ............................................. A61C 5/04
[52] U.S. Cl. ...................................................... 433/39
[58] Field of Search ............................. 433/39, 229, 3

[56] References Cited

U.S. PATENT DOCUMENTS

| | | | |
|---|---|---|---|
| 1,669,231 | 5/1928 | Curran | 433/39 |
| 1,688,670 | 10/1928 | Swendiman | 433/39 |
| 2,591,744 | 4/1952 | Tofflemire | 433/39 |
| 2,646,622 | 7/1953 | Christie et al. | 433/39 |
| 3,795,052 | 3/1974 | Mowery | 433/39 |
| 3,842,505 | 10/1974 | Eames | 433/39 |

FOREIGN PATENT DOCUMENTS 2278317  2/1976  France ................... 433/229

Primary Examiner—Gene Mancene
Assistant Examiner—David I. Tarnoff
Attorney, Agent, or Firm—Ziems, Walter & Shannon

[57] ABSTRACT

An improved dental matrix band of the general type having a central tooth circumscribing portion extending between cervical and occlusal edges and merging with a pair of arms adapted for engagement by a retainer appliance and to which a leaf-like flap is secured to the tooth engaging surface of the band to be deformable away from the band by a compressible wedge against the surface of a tooth to be filled. The flap has an inner edge generally coextensive with the cervical edge of the band and extends to an outer edge coextensive with or beyond the occlusal edge of the band. The flap is secured at only one corner either by a pair of spot welds to leave remaining the major area of the flap to be deflectable against the surface of a tooth. Alternatively, the flap is secured by a bendable neck portion integral with both the flap and the band.

14 Claims, 13 Drawing Figures

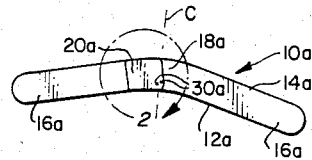
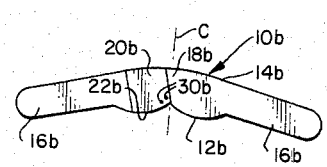
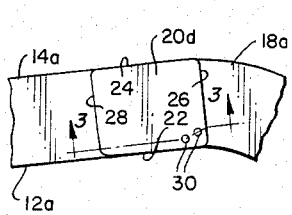
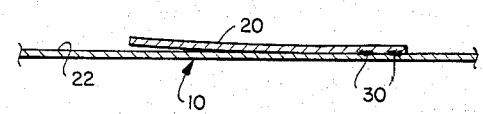
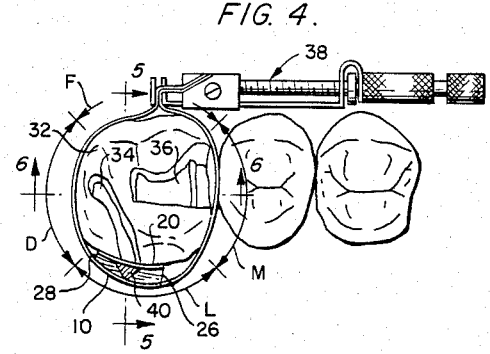
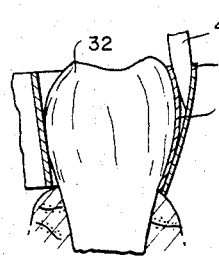
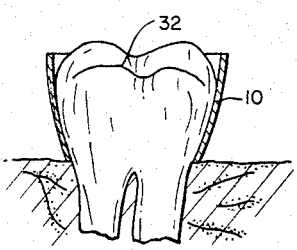

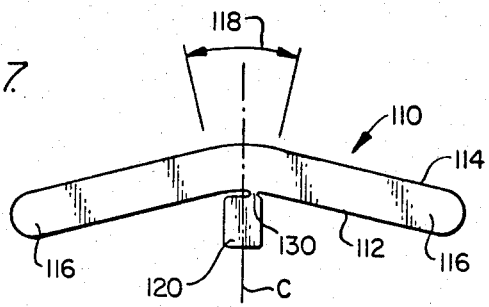
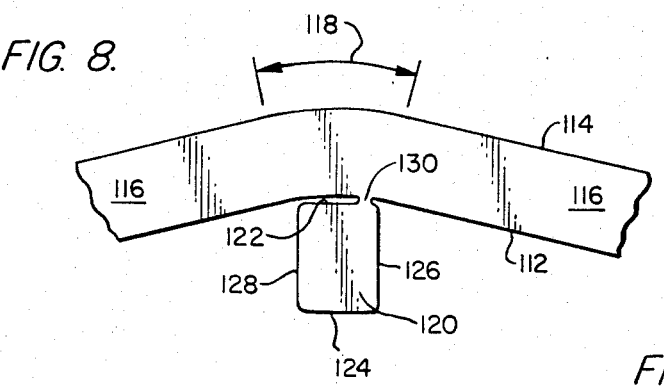
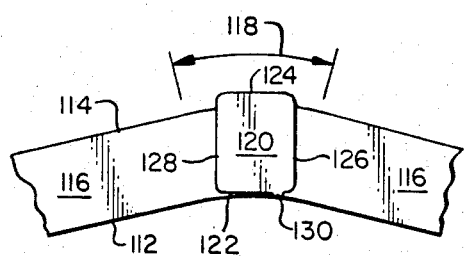
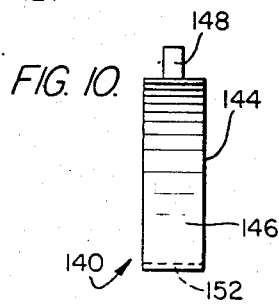
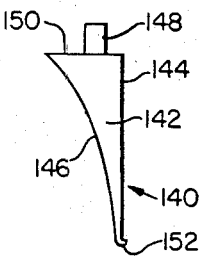
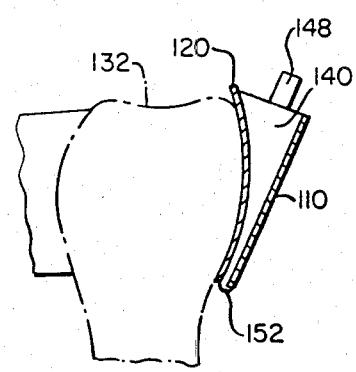

DENTAL MATRIX BAND

CROSS REFERENCE TO RELATED APPLICATION

This is a continuation-in-part of pending U.S. application Ser. No. 06/419,220, filed Sept. 17, 1982 now abandoned.

BACKGROUND OF THE INVENTION

1. Field of Invention

This invention relates to dental matrix bands and, more particularly, to improvements in such matrix bands by which the full vertical surface contour of a tooth may be accurately complemented by a mold surface so that the exterior surface of a filling compacted against such mold surface will be a smooth continuation of or lie flush with the original surface contour of the tooth.

2. Description of the Prior Art

Matrix bands are extensively used by dentists to fill cavities which open through any of the vertical surfaces of a tooth. Such bands are applied circumferentially about the crown of a tooth with the lateral dimension or width of the band extending from the cervical toward the occlusal surfaces of the tooth. Once in place, the band is placed under hoop stressing by a retaining appliance to provide a dam-like mold against which a filling material may be compacted. Conventional matrix bands as well as retaining appliances incident to their use are represented by the disclosures of U.S. Pat. Nos. 2,502,903; 2,538,486; 2,591,744; and 3,305,928, all issued to the inventor, B. F. Tofflemire.

Tofflemire-type matrix bands are formed of thin, foil-like metal having the characteristics of stainless steel and are shaped with an arcuate central portion merging tangentially with two linear arms capable of cooperation with the hoop stressing retainer appliance. When applied about a tooth crown, the arcuate central portion assumes a frusto-conical configuration conforming generally to the divergence of crown surfaces from the cervical. The frusto-conical shape of the placed matrix band insures a peripheral seal of the band at the cervical and is effective for compaction of filling material in fillings opening through surfaces at the mesial or front and distal or rear quadrants of a tooth crown. Cavities which open through lateral quadrants (lingual and facial surfaces) of the tooth, however, are not closed by the inner matrix band surfaces with the result that difficulty is encountered in the placement and compaction of filling material in such cavities.

The effectiveness of existing Tofflemire-type matrix bands in filling cavities which open to the mesial or distal surfaces of teeth is due in part because of the relatively predictable contour of these surfaces and also in part because of the availability of an adjacent tooth to act as a support for a wedge or pry by which the matrix band may be deflected against the tooth being filled. Surfaces on the lingual or facial sides of a tooth, however, are not only of more widely varying contour, but also are often reentrant as in the case of molars. In such cases, the hoop tension in the applied matrix band acts to hold the band spaced away from the concave reentrant portions of the exterior tooth surfaces to a point where it is difficult, if not impossible, to achieve the degree of compaction necessary at the original surface contour of the tooth. Attempts have been made at solutions to this problem by providing a matrix band with a preformed concavity (U.S. Pat. No. 3,842,505—Wilmer B. Eames) or by retainers for compressing the matrix band against the tooth exterior (U.S. Pat. No. 2,646,622—D. R. Christy et al.). Such approaches to the problem, however, have not been totally satisfactory due to the difficulty of accommodating varying contours as in the case of the preformed matrix band or by a compromise in the availability of hoop tensioning. It is apparent, therefore, that improvements are needed in dental matrix bands to achieve a complementary mold surface for the complete exterior crown surfaces of a tooth.

SUMMARY OF THE INVENTION

In accordance with the present invention, the problems heretofore encountered as a result of nonconformance by matrix band molding surfaces with exterior tooth surface contours are substantially overcome by the attachment to the molding surface of a conventional matrix band of a leaf-like flap approximating the thickness of the matrix band. The flap is secured at one corner thereof to the cervical edge of the band thus leaving the remaining area of the flap free to be deflected or deformed away from the matrix band by an appropriate shim into engagement with the exterior surface of a tooth enveloped or circumscribed by the matrix band.

The leaf-like flap may be incorporated as an adjunct to an existing band by spot welding a corner of the flap to a point near the cervical edge of the band. Alternatively and preferably, the flap is integrated with the band by a foldable neck portion so that the band and flap may be formed as a one-piece stamping and the flap folded over either side of the band. In use, the band, with the flap located toward the tooth, is loosely positioned. A shim is then placed between the flap and the band so that upon tightening the band, unsecured portions of the flap will be deformed away from the inner surface of the band and firmly against the exterior of a tooth to be filled. The shim is preferably a shaped molding of resilient plastic but other readily available devices, such as a toothpick or a piece of hard dental wax may be used.

A principal object of the present invention, therefore, is to provide an improved dental matrix band to facilitate filling of cavities opening particularly through the facial or lingual surfaces of a tooth crown. Other objects and further scope of applicability of the present invention will become apparent from the detailed description to follow taken in conjunction with the accompanying drawings in which like parts are designated by like reference numerals.

BRIEF DESCRIPTION OF THE DRAWINGS

FIGS. 1A and 1B are plan view illustrations of conventional matrix bands incorporating the improvement of the present invention;

FIG. 2 is an enlarged fragmentary plan view corresponding to the area circumscribed by the circular sight line 2 in FIG. 1A;

FIG. 3 is an enlarged fragmentary cross-section on line 3—3 of FIG. 2;

FIG. 4 is a plan view illustrating the improved matrix band of the present invention in place about a tooth;

FIG. 5 is a cross-section on line 5—5 of FIG. 4;

FIG. 6 is a cross-section on line 6—6 of FIG. 4;

FIG. 7 is a plan view of an alternative embodiment of the invention;

FIG. 8 is an enlarged plan view illustrating a fragment of the embodiment of FIG. 7;

FIG. 9 is a view, like FIG. 8, but with the device in a condition for use;

FIG. 10 is a front elevation of a preferred type of shim usable with the matrix band of the inventions;

FIG. 11 is a side elevation of the shim shown in FIG. 10; and

FIG. 12 is a cross-section similar to FIG. 5 but illustrating the alternative embodiment of FIG. 7.

DETAILED DESCRIPTION OF THE PREFERRED EMBODIMENTS

In FIGS. 1A and 1B of the drawings, the present invention is shown as an adaptation to alternative shapes of dental matrix bands 10a and 10b. The bands 10 per se, are conventional Tofflemire-type matrix bands and as such are constituted structurally as a strip of foil-like metal, such as stainless steel, having a generally symmetrical configuration longitudinally with respect to a center line C. The shapes of the bands 10a and 10b are similar to the extent that each defines a cervical edge 12a, 12b, an occlusal edge 14a, 14b, and a pair of arms 16a, 16b extending in tangential fashion from an arcuate central section 18a, 18b. The bands differ principally in that the cervical edge 12b of the band 10b is shaped to define a pair of arcuate projections whereas the cervical edge of the band 10a generally parallels the occlusal edge 14a thereof. The alternative shapes of matrix bands configurations illustrated in FIGS. 1A and 1B are not inclusive of all shapes of matrix bands to which the present invention is applicable but are intended as representative of varying shapes of dental matrix bands currently in use.

In accordance with one embodiment of the present invention, dental matrix bands of the type represented in FIGS. 1A and 1B are modified to include a leaf-like flap 20 of metal foil having essentially the same physical characteristics as the metal from which the bands are formed. The shape and relative dimensions of the flap 20a are shown most clearly in FIGS. 2 and 3 to be of a generally rectangular peripheral configuration and in this embodiment, is dimensioned so that the inner and outer edges 22 and 24 of the flap are substantially coextensive respectively with the cervical and occlusal edges 12a and 14b of the matrix band 10a. In the matrix band 10b, the inner edge 22b of the flap 20b is curved to be coextensive with the curved cervical edge 12b. In both instances, the length of the flap between leading and trailing end edges 26 and 28, respectively, approximates one-half to three-quarters of the arcuate central section 18 of the matrix band 10.

The flap 20 is secured to the band 10 near the center thereof only at a relatively small area or spot to leave the major area of the flap free to be deflected away from the band. In the embodiment shown in FIGS. 1-6, the securement is effected by two spot welds 30 located in the region of the corner of the flap defined by the inner edge 22 and the leading end 26. The provision of two spot welds develops a reaction couple in the connection of the flap to the band 10 in a manner such that accidental dislodgement of the flap, as might occur by torsion at only one such spot weld, is prevented.

An understanding of the manner in which the improved matrix band of the present invention is used in practice may be gained by reference to FIGS. 4-6 of the drawings. In FIG. 4, a matrix band 10 including the flap 20 is shown in place about a molar 32 having two cavities 34 and 36 prepared to receive a filling material (not shown). For purposes of reference only, the molar 32 may be considered as having four substantially equal quadrants designated in FIG. 4 by the arcuate arrows M, L, D and F which quadrants represent, respectively, the mesial, lingual, distal, and facial surfaces of the tooth 32. In the illustrated example, the cavity 36, therefore, opens to the mesial surface M whereas the cavity 34 opens to the lingual surface of the tooth 34.

The band 20 is retained circumferentially about the tooth 32 using a conventional Tofflemire-type retaining appliances 38 by which the band 10 may be clamped under circumferential tension about the vertical surfaces of a tooth. Also the retaining clamp appliance 38 may be located on either the facial or lingual sides of the tooth but always on the opposite side of the tooth from the surface in which a cavity to be filled is located. Also, it will be noted in FIGS. 4 and 6 that a cavity opening either to the mesial or the distal quadrants such as the cavity 36, is closer to the cervical of the tooth principally because of the usual need to extend the opening to remove decay commonly found in this area. The cavity 34 in the illustrated example, however, is relatively remote from the cervical and often beyond the height of contour or in a region where the surface of the tooth curves inwardly after a divergence outwardly from the cervical. It is this latter type of cavity to which the present invention is primarily addressed.

Also FIG. 4, the dimensional relationship of the flap 20 and the molar 32 may be observed. It will be noted, for example, that because the length of the flap 20 between the leading and the trailing edges 26 and 28 thereof less than the arcuate central section 18 of the matrix band 10, the band may be applied to the molar 32 so that the trailing edge 28 of the flap 20 does not encroach on the distal quadrant D (or the mesial quadrant M where the connection of the flap 20 to the band 10 is reversed). It is important that the flap 20 does not extend into the mesial or distal quadrants because the point of junction thereof with the primary band 10 will cause a wrinkle in the surface of a mesial or distal restoration packed against it.

As may be seen in FIG. 5 of the drawings, the flap 20 may be deflected inwardly against the surface of the lingual or facial surfaces of the tooth 32 simply by the insertion of a wedge or shim 40 between the band 10 and the flap 20 prior to final tightening of the band 10. The shim 40 may be a toothpick (as illustrated) or a piece of hard dental wax and functions to retain the flap 20 firmly against the exterior surface of the tooth through which a cavity like the cavity 34 opens after the band 10 is tightened by the appliance 8. As a result, the cavity 34 may be filled and compacted uniformly throughout including the region adjacent the outer surface of the tooth. Because of this facility for compaction throughout, the resulting filling is substantially stronger than fillings defined by a matrix band spaced from the exterior of the surface of the tooth and subsequently ground or removed back to the surface of the tooth.

In FIG. 7-12 of the drawings, an alternative embodiment of the invention is illustrated in which parts corresponding to parts identified in the embodiment of FIGS. 1-6 are designated by the same reference numerals in a one-hundred series. The principal difference between the embodiment of FIGS. 7-12 and the embodiment previously described is that the flap 120 in the latter embodiment is formed as an integral appendage to the band 110. As a result, the band 110 and the flap 120 may be stamped simultaneously from a sheet of stock material such as foil-like stainless steel and thus facilitate manufacture of the assembly with significantly reduced costs.

The flap 120 is joined at one corner with the cervical edge 112 of the band 110 by a neck portion 130. The location of the neck 130 near the leading edge 126 of the flap 120 permits a major portion of the cervical or inner edge 122 of the flap to be free for displacement away from the cervical edge 112 of the band. The relatively narrow width of the neck portion 130 allows the flap 120 to be folded against either one or the other of opposite sides of the band and additionally, to be adjusted angularly by flexing the metal at the neck to enable positioning of the flap on the area represented by the arcuate central portion 118 of the band.

It will be noted further with respect to the embodiment of FIGS. 7-12 that the flap 120 is located centrally on the arcuate portion 118 of the band and assumes approximately three-quarters of the length of the central arcuate portion 118. This facilitates placement of the flap against any portion of the lingual or facial quadrants of a molar without concern for extension of the flap into the distal or mesial quadrants of the molar.

A still further advantageous feature incorporated in the embodiment of FIGS. 7-12 is that the height of the flap 120 or the distance between the cervical or inner edge 122 and the occlusal or outer edge 124 thereof is greater than the width of the arcuate portion 118 of the band 110. as may be seen in FIG. 12, this extension of the flap 120 facilitates a separation of the occlusal edges of the flap and of the band for insertion of a shim 140.

The shim 140 is illustrated fully in FIGS. 10 and 11 to include a generally wedge-shaped body portion 142 having a substantially linear outer surface 144 and a concave, smoothly curved inner surface 146. A handling stud 148 projects from the top surface 150 to enable the shim 140 to be retained by a tweezers (not shown). A positioning lip 152 is provided on the bottom edge of the body portion 142 to engage under the cervical edge 112 of the band 114.

The shim 140 is preferably molded of resilient plastic material such as polyethylene so that departures made by a tooth contour from the arcuate surface 146 will be accommodated by resiliency of the material from which the shim 140 is molded.

Thus it will be appreciated that as a result of the present invention an improved dental matrix band is provided by which the stated objective among others are fulfilled. Also, it will be understood from the preceding description that modifications may be made in the illustrated embodiments without departure from the invention. Accordingly, it is expressly intended that the foregoing description and accompanying drawings are illustrative only, not limiting, and that the true spirit and scope of the present invention is to be determined by reference to the appended claims.

I claim:

1. In a dental matrix band having a central tooth circumscribing portion with a tooth engaging surface extending between cervical and occlusal edges, the central portion merging with a pair of arms adapted for engagement by a retainer appliance, the improvement comprising:

a leaf-like flap secured to said central portion and adapted to overlie the tooth engaging surface thereof, said flap being deformable away from said tooth engaging surface against the surface of a tooth to be filled.

2. The apparatus recited in claim 1, wherein said flap has an inner edge substantially coextensive with the cervical edge of the central portion of the band, and extends at least to the occlusal edge of said central portion.

3. The apparatus recited in claim 2 wherein said flap extends from said inner edge to an outer edge located beyond the occlusal edge of said central portion of the band.

4. The apparatus recited in either of claims 1, 2 or 3, wherein said flap extends longitudinally between leading and trailing edges, the distance between said leading and trailing edges being from one-half to three-quarters the length of said central portion.

5. The apparatus recited in claim 4, wherein said flap is secured to the matrix band over a relatively small area near the cervical edge of the matrix band.

6. The apparatus recited in claim 5, wherein the matrix band and said flap are formed of thin metal having the characteristics of stainless steel.

7. The apparatus recited in claim 6, wherein said flap is secured to the matrix band by a pair of spaced spot welds.

8. The apparatus recited in claim 7, said spot welds are located at the corner defined by the leading and inner edges of said flap.

9. The apparatus recited in claim 5 wherein said flap is secured to the matrix band by a bendable neck portion.

10. The apparatus recited in claim 9 wherein said flap is initially coplanar with the matrix band and adapted to be positioned against either of opposite sides of the band by bending said neck portion.

11. In a dental matrix band having a central tooth circumscribing portion with a tooth engaging surface extending between cervical and occlusal edges, the central portion merging with a pair of arms adapted for engagement by a retainer appliance, the improvement comprising in combination:

a leaf-like flap secured to said central portion and adapted to overlie the tooth engaging surface thereof, said flap being deformable away from said tooth engaging surface against the surface of a tooth to be filled; and a shim adapted for insertion between said flap and said tooth engaging surface.

12. The combination recited in claim 11 wherein said shim is molded from resilient plastic material.

13. The combination recited in claim 11 wherein said shim includes a wedge-shaped body portion having a substantially linear outer edge and a curved, concave inner surface.

14. The combination recited in claim 13 wherein said shim includes a handling stud at the top of said body portion and a positioning lip at the bottom edge thereof to engage the cervical edge of the band.

* * * * *